(12) United States Patent
Matsumura et al.

(10) Patent No.: US 10,881,329 B2
(45) Date of Patent: Jan. 5, 2021

(54) MOTION DISPLAY SYSTEM AND RECORDING MEDIUM

(71) Applicant: Panasonic Intellectual Property Management Co., Ltd., Osaka (JP)

(72) Inventors: Yoshihiro Matsumura, Osaka (JP); Tomoharu Nakahara, Hyogo (JP); Tomohiko Fujita, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 463 days.

(21) Appl. No.: 15/813,602

(22) Filed: Nov. 15, 2017

(65) Prior Publication Data

US 2018/0070863 A1 Mar. 15, 2018

Related U.S. Application Data

(63) Continuation of application No. PCT/JP2016/002486, filed on May 23, 2016.

(30) Foreign Application Priority Data

Jun. 1, 2015 (JP) ................................ 2015-111751

(51) Int. Cl.
*A61B 5/11* (2006.01)
*G06T 11/60* (2006.01)
(Continued)

(52) U.S. Cl.
CPC .......... *A61B 5/1127* (2013.01); *A61B 5/0077* (2013.01); *A61B 5/112* (2013.01);
(Continued)

(58) Field of Classification Search
CPC ... A61B 5/1127; A61B 5/1128; A61B 5/0077; A61B 5/112; A61B 5/6823;
(Continued)

(56) References Cited

U.S. PATENT DOCUMENTS

2006/0204045 A1\* 9/2006 Antonucci ......... G06K 9/00342
382/107
2013/0120445 A1 5/2013 Shimomura et al.
(Continued)

FOREIGN PATENT DOCUMENTS

| CN | 102860841 A | 1/2013 |
| CN | 103025241 A | 4/2013 |

(Continued)

OTHER PUBLICATIONS

Tao et al., "Integration of Vision and Inertial Sensors for 3D Arm Motion Tracking in Home-based", Jun. 2007, Sage Publications, The International Journal of Robotics Research, vol. 26, No. 6, p. 607-624. (Year: 2007).\*

(Continued)

*Primary Examiner* — Vincent Rudolph
*Assistant Examiner* — Timothy Choi
(74) *Attorney, Agent, or Firm* — McDermott Will & Emery LLP

(57) ABSTRACT

A motion display system includes: a detector that detects an acceleration of a body part of a test subject; an imager that generates a moving image by imaging a motion of the test subject; an identifier that is attached to the test subject to determine a position of the body part within the moving image; a superimposer that superimposes a motion trajectory of the body part generated based on the acceleration detected by the detector on a position of the body part determined based on the identifier within the moving image generated by the imager in synchronization with the moving image; and a display that displays the moving image on which the motion trajectory is superimposed by the superimposer.

8 Claims, 9 Drawing Sheets

(51) Int. Cl.
*G06T 11/00* (2006.01)
*G06T 11/20* (2006.01)
*A61B 5/00* (2006.01)

(52) U.S. Cl.
CPC .......... *A61B 5/6823* (2013.01); *A61B 5/6831* (2013.01); *A61B 5/7271* (2013.01); *A61B 5/743* (2013.01); *G06T 11/00* (2013.01); *G06T 11/206* (2013.01); *G06T 11/60* (2013.01); *A61B 5/1116* (2013.01); *A61B 2562/0219* (2013.01)

(58) Field of Classification Search
CPC ..... A61B 5/6831; A61B 5/7271; A61B 5/743; A61B 5/1116; A61B 2562/0219; G06T 11/00; G06T 11/206; G06T 11/60; G06K 9/00342; G06K 9/00348
See application file for complete search history.

(56) References Cited

U.S. PATENT DOCUMENTS

| | | | |
|---|---|---|---|
| 2013/0123669 A1 | 5/2013 | Kinoshita et al. | |
| 2015/0325004 A1 | 11/2015 | Utsunomiya et al. | |
| 2016/0030808 A1* | 2/2016 | Uchida | G09B 19/0038 482/8 |
| 2016/0048993 A1 | 2/2016 | Shimomura et al. | |
| 2018/0325467 A1* | 11/2018 | Matsumura | A61B 5/743 |

FOREIGN PATENT DOCUMENTS

| | | |
|---|---|---|
| JP | 2007-226761 A | 9/2007 |
| JP | 2009-017895 A | 1/2009 |
| JP | 2013-103010 A | 5/2013 |
| JP | 2014-128409 A | 7/2014 |
| JP | 2015-042241 A | 3/2015 |
| WO | 2007/052631 A1 | 5/2007 |

OTHER PUBLICATIONS

Xu et al., "Analysis of Human Gait Bilateral Symmetry for Functional Assessment after an Orthopaedic Surgery", Jul. 2009, Springer-Verlag, 6th Int. Conf. Image Analysis and Recognition ICIAR 2009, LNCS vol. 5627, p. 627-636. (Year: 2009).*

Moiz et al., "A Wearable Motion Tracker", Sep. 2010, ACM, Proceedings of the 5th Int. Conf. on Body Area Networks, p. 214-219. (Year: 2010).*

Yoneyama et al., "Accelerometry-Based Gait Analysis and its Application to Parkinson's Disease Assessment—Part 1: Detection of Stride Event", May 2014, IEEE, Transactions on Neural Systems and Rehabilitation Engineering, vol. 22, No. 3, p. 613-622. (Year: 2014).*

Choi et al., "A computerized program for three-dimensional visualization and quantitative analysis of cell nuclei", Jun. 2004, IEEE, Proceedings of 6th Int. Workshop on Enterprise Networking and Computing in Healthcare Industry—Healthcom 2004, p. 83-87. (Year: 2004).*

Bleser et al., "Advanced tracking through efficient image processing and visual-inertial sensor fusion", Feb. 2009, Elsevier, Computers & Graphics, vol. 33, is. 1, p. 59-72. (Year: 2009).*

Chinese Office Action with Search Report issued in corresponding Chinese Application No. 201680027808.6, dated Oct. 30, 2019, with partial English translation.

International Search Report issued in Application No. PCT/JP2016/002486 dated Aug. 2, 2016, with English translation.

* cited by examiner

MOTION DISPLAY SYSTEM AND RECORDING MEDIUM

CROSS REFERENCE TO RELATED APPLICATIONS

This application is a U.S. continuation application of PCT International Patent Application Number PCT/JP2016/002486 filed on May 23, 2016, claiming the benefit of priority of Japanese Patent Application Number 2015-111751 filed on Jun. 1, 2015, the entire contents of which are hereby incorporated by reference.

BACKGROUND

1. Technical Field

The present disclosure relates to a motion display system, and a recording medium.

2. Description of the Related Art

Conventionally, a technique is known in which an acceleration sensor is attached to a subject (test subject) and a motion of the subject is analyzed based on acceleration data detected by the acceleration sensor (see, for example, WO 2007/052631). For example, WO 2007/052631 discloses that the acceleration vector data obtained from the acceleration sensor is rendered on a plane.

However, with the conventional technique described above, although it is possible to determine a motion of the body part to which the acceleration sensor is attached based on the acceleration vector data, it is not possible to determine a posture of the test subject while he/she is making the motion. For example, a walking posture and the motion of the body part to which the acceleration sensor is attached cannot be distinguished, and it is therefore difficult to determine the actual motion of the test subject.

SUMMARY

Accordingly, it is an object of one aspect of the present disclosure to provide a motion display system and the like that enable a motion of a test subject to be visually recognizable.

In order to achieve the above object, a motion display system according to one aspect of the present disclosure includes: an acceleration sensor that detects an acceleration of a body part of a test subject; an imager that generates a moving image by imaging a motion of the test subject; an identifier that is attached to the test subject to determine a position of the body part within the moving image; a superimposer that superimposes a motion trajectory of the body part generated based on the acceleration detected by the acceleration sensor on a position of the body part determined based on the identifier within the moving image generated by the imager in synchronization with the moving image; and a display that displays the moving image on which the motion trajectory is superimposed by the superimposer.

Also, the one aspect of the present disclosure can also be implemented as a program for causing a computer to function as the motion display system described above. Alternatively, the one aspect of the present disclosure can also be implemented as a computer-readable recording medium in which the above program is stored.

The motion display system and the like according to the present disclosure enable a motion of a test subject to be visually recognizable.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF THE EMBODIMENTS

Figure 1:
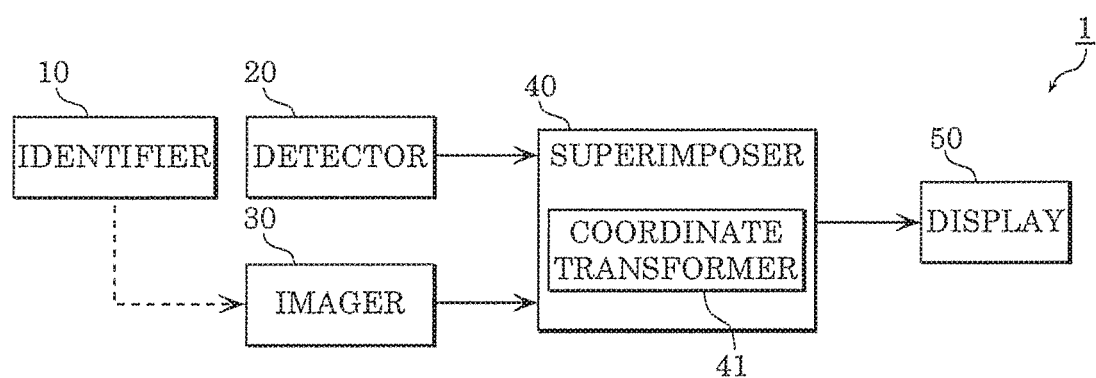
FIG. 1 is a block diagram showing a functional configuration of a motion display system according to Embodiment 1.

Hereinafter, motion display systems according to embodiments of the present disclosure will be described in detail with reference to the drawings. Note that the embodiments described below show specific examples of the present disclosure. Accordingly, the numerical values, shapes, materials, structural elements, the arrangement and connection of the structural elements, steps, the order of the steps, and the like shown in the following embodiments are merely examples, and therefore do not limit the scope of the present disclosure. Accordingly, among the structural elements described in the following embodiments, structural elements not recited in any one of the independent claims are described as arbitrary structural elements.

In addition, the diagrams are schematic representations, and thus are not necessarily true to scale. Also, in the diagrams, structural elements that are the same are given the same reference numerals.

Embodiment 1

[Action Display System]

An overview of a motion display system according to the present embodiment will be described first with reference to FIGS. 1 to 3.

FIG. 1 is a block diagram showing a functional configuration of motion display system 1 according to the present embodiment. FIG. 2 is a schematic diagram showing a specific configuration of motion display system 1 according to the present embodiment. FIG. 3 is a diagram showing test subject 200 to which acceleration sensor 120 according to the present embodiment is attached. In FIG. 1, a dashed arrow indicates that identifier 10 is imaged by imager 30, and solid arrows indicate the flow of signals (information) between structural elements. The same applies to FIG. 8, which will be described later.

As shown in FIG. 1, motion display system 1 includes identifier 10, detector 20, imager 30, superimposer 40, and display 50. Also, as shown in FIG. 2, motion display system 1 includes, in order to implement the functions of processors shown in FIG. 1, belt 100, video camera 130, computer 140, and display 150. Belt 100 includes reflector 110 and acceleration sensor 120.

Hereinafter, the structural elements of motion display system 1 will be described in detail with reference to the drawings.

[Identifier]

Identifier 10 is attached to test subject 200, and is used to determine the position of a predetermined body part of test subject 200 within a moving image. That is, identifier 10 functions as a mark within the moving image. The predetermined body part refers to an area to which acceleration sensor 120 is attached (hereinafter referred to as "sensor-attached body part").

Figure 2:
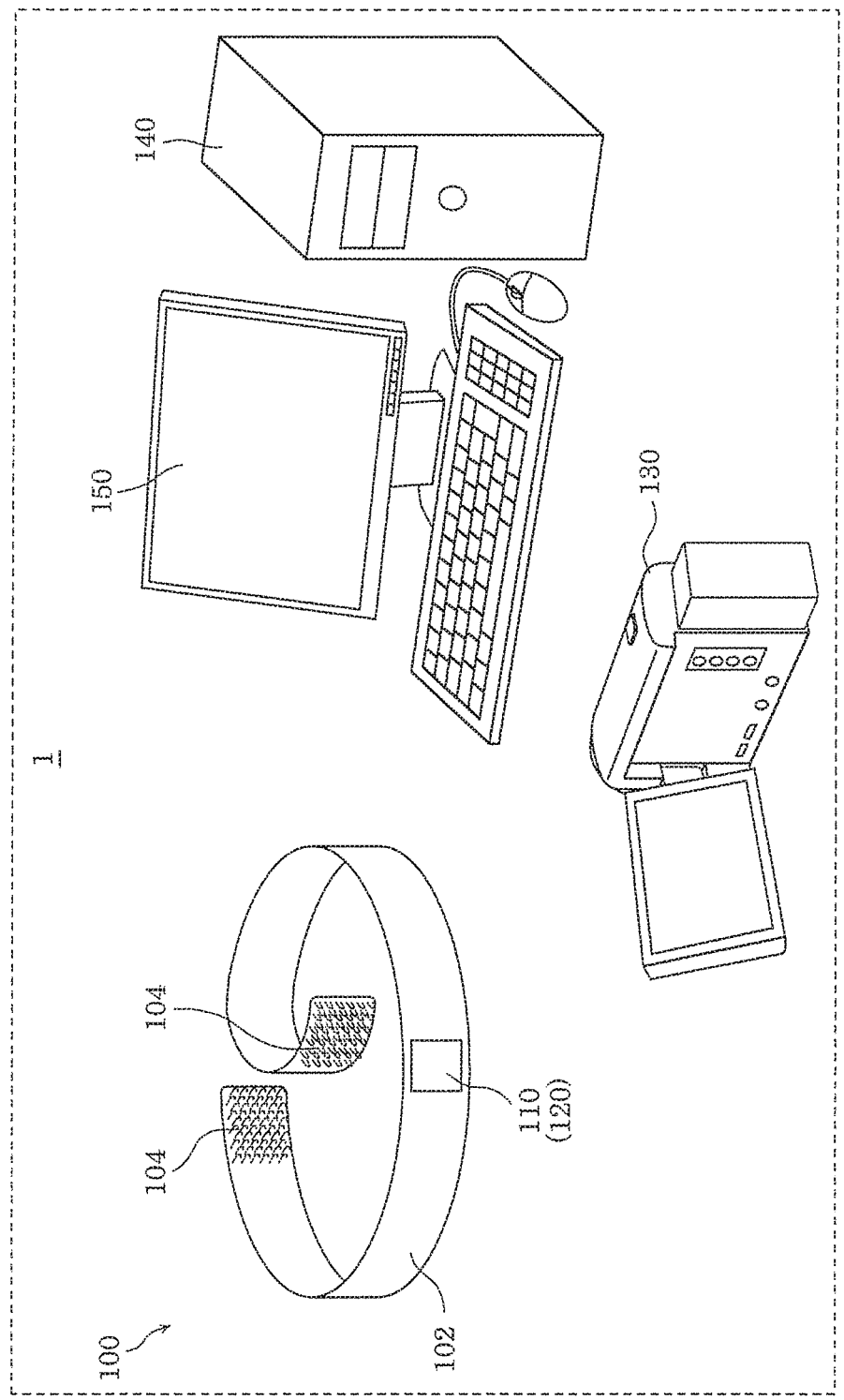
FIG. 2 is a schematic diagram showing a specific configuration of the motion display system according to Embodiment 1.

In the present embodiment, identifier 10 is reflector 110 shown in FIG. 2. Alternatively, identifier 10 may be a color marker. Reflector 110 serves as a mark for determining the sensor-attached body part to which acceleration sensor 120 is attached within a moving image when test subject 200 is imaged by imager 30. Reflector 110 is fixed in a relative position respect to the sensor-attached body part to which acceleration sensor 120 is attached. To be specific, reflector 110 is provided on a surface of acceleration sensor 120. That is, the position of reflector 110 corresponds to the position of the sensor-attached body part to which acceleration sensor 120 is attached.

For example, reflector 110 can be a name plate of acceleration sensor 120. Alternatively, as identifier 10, a color marker may be applied to the name plate of acceleration sensor 120. The color marker is a marker having a predetermined color. For example, the color marker has a color different from the color of the clothes worn by test subject 200.

[Detector]

Detector 20 detects the acceleration of the predetermined body part of test subject 200. Detector 20 outputs the detected acceleration to superimposer 40. Detector 20 detects the acceleration at a predetermined detection rate (the number of times of detection of acceleration per unit time) and outputs the detected acceleration to superimposer 40. Time-series data representing a variation in acceleration with time is thereby input into superimposer 40.

In the present embodiment, detector 20 is acceleration sensor 120 shown in FIG. 2. Acceleration sensor 120 is, for example, a three-axis acceleration sensor, and generates three-dimensional acceleration vector data.

Acceleration sensor 120 performs communication with computer 140. Acceleration sensor 120 transmits the generated acceleration vector data to computer 140 through, for example, wireless communication. The wireless communication is performed based on predetermined wireless communication standards such as, for example, Bluetooth®, Wi-Fi®, or ZigBee®.

The acceleration vector data includes time information (time stamp). The time information indicates the time when the acceleration was detected. The time information may indicate the time when the acceleration vector data was received by computer 140 from acceleration sensor 120.

The detection rate of acceleration sensor 120 is set to be, for example, the same as the frame rate of the moving image imaged by video camera 130. By doing so, it is possible to easily superimpose a motion trajectory, which will be described later, on the moving image. It is to be noted that the acceleration detection rate may be different from the frame rate of the moving image. Each of the acceleration vector data and the moving image includes time information, and thus the motion trajectory and the moving image may be synchronized by using the time information so as to perform superimposition.

[Belt]

A configuration for attaching reflector 110 and acceleration sensor 120 to test subject 200 will now be described. In the present embodiment, as shown in FIG. 2, belt 100 includes reflector 110 and acceleration sensor 120. As a result of test subject 200 wearing belt 100, it is possible to attach reflector 110 to test subject 200 and also attach acceleration sensor 120 to a predetermined body part of test subject 200.

Belt 100 is an example of an attachment member for attaching reflector 110 and acceleration sensor 120 to test subject 200. As shown in FIG. 2, belt 100 includes strap 102 and hook-and-loop fastener 104.

Strap 102 is an elongated strip or string, which is fixed by being wound around the waist, the arm, the head, the leg, or the like of test subject 200. There is no particular limitation on the material of strap 102, but strap 102 is made of a material that is different from that of reflector 110 (or the color marker), and has a color different from that of reflector 110 (or the color marker).

Hook-and-loop fastener 104 is an example of a fixture for fixing strap 102. Hook-and-loop fastener 104 has a loop surface and a hook surface, which are respectively provided on two end portions of strap 102. By joining the loop surface and the hook surface together, the length of strap 102 is adjusted so as to fix belt 100 to test subject 200.

Here, an example was described in which hook-and-loop fastener 104 is used as means for fixing strap 102, but the present disclosure is not limited thereto. Belt 100 may include a buckle instead of hook-and-loop fastener 104.

Figure 3:
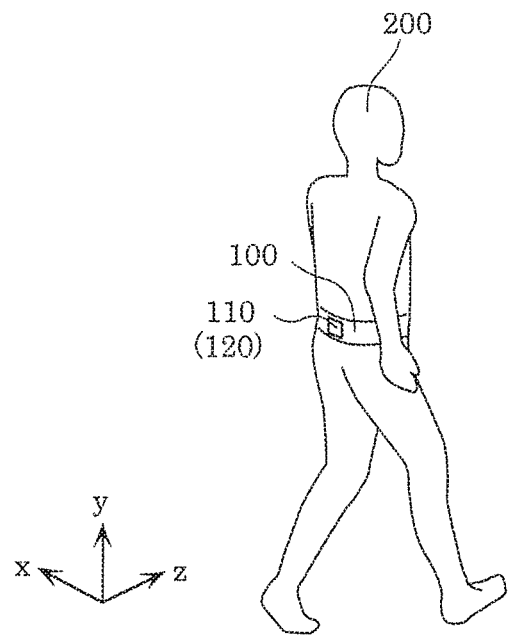
FIG. 3 is a diagram showing a test subject to which an acceleration sensor according to Embodiment 1 is attached.

FIG. 3 is a diagram showing test subject 200 to which acceleration sensor 120 according to the present embodiment is attached.

In the example shown in FIG. 3, as a result of belt 100 being worn around the waist of test subject 200, acceleration sensor 120 and reflector 110 are attached to the back side of the waist of test subject 200. The sensor-attached body part that is the location to which acceleration sensor 120 and reflector 110 are attached is not limited to the waist, and may be the arm, the head, the leg, or the like.

In the present embodiment, acceleration sensor 120 is attached to test subject 200 by using belt 100, but the present disclosure is not limited thereto. For example, acceleration sensor 120 may include an attachment element such as a hook-and-loop fastener, a safety pin, or a clip. Acceleration sensor 120 may be attached to test subject 200 by using such an attachment element. Alternatively, acceleration sensor 120 may be placed in a pocket or the like of the clothes worn by test subject 200. At this time, identifier 10 such as reflector 110 may be attached to the outer surface or the like of the pocket.

[Imager]

Imager 30 images the motion of test subject 200 and generates a moving image. To be specific, imager 30 images test subject 200 such that identifier 10 (reflector 110) is imaged. Identifier 10 need not be imaged constantly. If identifier 10 is not imaged in a predetermined frame of the moving image, superimposer 40 may estimate the position of identifier 10 in the predetermined frame by using, for example, the previous and subsequent frames of the predetermined frame.

In the present embodiment, imager 30 is video camera 130. Video camera 130 is capable of, for example, performing operations such as panning, tilting, and zooming according to the motion of test subject 200. Video camera 130 performs imaging focusing on, for example, test subject 200.

Video camera 130 performs communication with computer 140 (or display 150). Video camera 130 transmits the generated moving image data to computer 140 through, for example, wireless communication. The wireless communication is performed based on predetermined wireless communication standards such as, for example, Bluetooth, Wi-Fi, or ZigBee. Video camera 130 may perform communication with computer 140 in a wired manner such as through a LAN (Local Area Network) cable.

[Superimposer]

Superimposer 40 superimposes a motion trajectory of the sensor-attached body part generated based on the acceleration detected by acceleration sensor 120 on the position of the sensor-attached body part determined based on identifier 10 within the moving image generated by imager 30, in synchronization with the moving image.

In the present embodiment, superimposer 40 generates a motion trajectory based on the acceleration data transmitted from acceleration sensor 120. To be specific, superimposer 40 determines the amount of displacement and the direction of movement from a reference position of the predetermined body part by using the detected acceleration. The reference position is set to, for example, the sensor-attached body part to which acceleration sensor 120 is attached when test subject 200 is stationary. Superimposer 40 generates a motion trajectory by continuously rendering the amount of displacement and the direction of movement that have been determined onto a three-dimensional coordinate system or a two-dimensional coordinate system in a time-series manner.

Figure 4:
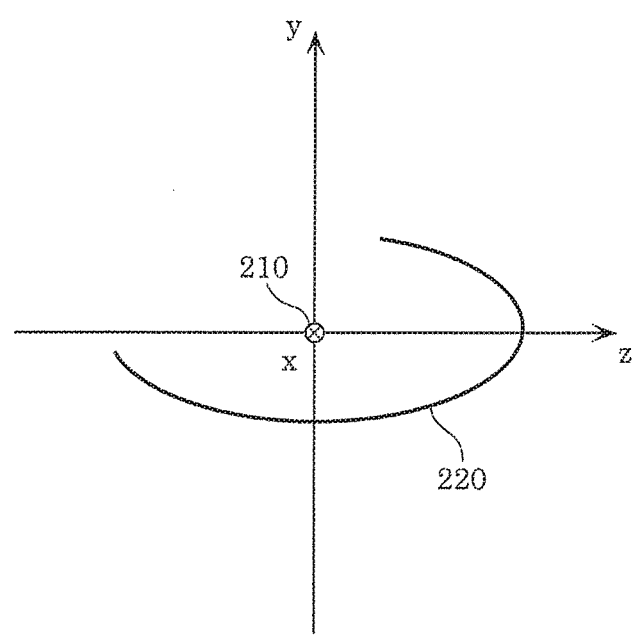
FIG. 4 is a diagram showing a motion trajectory of a predetermined body part generated based on acceleration data detected by the acceleration sensor according to Embodiment 1.

FIG. 4 is a diagram showing motion trajectory 220 of the predetermined body part generated based on the acceleration data detected by acceleration sensor 120 according to the present embodiment. In FIG. 4, motion trajectory 220 is expressed in a two-dimensional coordinate system.

The two-dimensional coordinate system is, specifically, a coronal plane (xy plane), a sagittal plane (yz plane), a horizontal plane (xz plane) or the like with respect to test subject 200. In the present embodiment, motion trajectory 220 is expressed on the sagittal plane. That is, in FIG. 4, x axis indicates the right left direction of test subject 200, y axis indicates the up down direction (i.e., vertical direction) of test subject 200, and z axis indicates the front rear direction of test subject 200.

In the present embodiment, superimposer 40 generates a motion trajectory in a two-dimensional coordinate system in order to superimpose the motion trajectory on the moving image. Alternatively, superimposer 40 may coordinate-transform the motion trajectory generated in a three-dimensional coordinate system to a two-dimensional coordinate system.

As shown in FIG. 1, superimposer 40 includes coordinate transformer 41.

Coordinate transformer 41 coordinate-transforms motion trajectory 220 such that a specific point in the coordinate system of motion trajectory 220 is set to a fixed point of test subject 200 within the moving image. For example, the specific point is origin point 210 of the coordinate system of motion trajectory 220, and the fixed point is the position of the sensor-attached body part to which acceleration sensor 120 is attached within the moving image.

In the present embodiment, coordinate transformer 41 determines the fixed point within the moving image based on the position of reflector 110 within the moving image, and coordinate-transforms motion trajectory 220 such that the specific point is set to the fixed point that has been determined. For example, reflector 110 reflects light, and thus an area corresponding to reflector 110 has a higher brightness value than the other area. Accordingly, coordinate transformer 41 can determine, by comparing the pixel values within the moving image with a predetermined threshold value, an area within the moving image where the brightness value is higher than the threshold value as the position of reflector 110.

In the case where a color marker is used instead of reflector 110, coordinate transformer 41 can determine the position of the color marker by detecting the color of the color marker from the moving image.

Coordinate transformer 41 determines the position of the sensor-attached body part to which acceleration sensor 120 is attached as the fixed point based on the determined position of reflector 110. In the present embodiment, the position of reflector 110 corresponds to the position of the sensor-attached body part to which acceleration sensor 120 is attached, and thus coordinate transformer 41 determines the position of reflector 110 as the fixed point.

In the case where the position of reflector 110 is different from the position of the sensor-attached body part to which acceleration sensor 120 is attached, coordinate transformer 41 determines the position of the sensor-attached body part to which acceleration sensor 120 is attached from the position of reflector 110 based on the positional relationship between acceleration sensor 120 and reflector 110. To be specific, coordinate transformer 41 acquires the direction from reflector 110 to acceleration sensor 120 and the distance from reflector 110 to acceleration sensor 120 based on user input, a still image of test subject 200, or the like. Coordinate transformer 41 calculates the position of acceleration sensor 120 by adding the acquired direction and distance to the position of reflector 110.

Coordinate transformer 41 coordinate-transforms motion trajectory 220 such that origin point 210 of the coordinate system of motion trajectory 220 matches the thus-determined fixed point (the sensor-attached body part to which acceleration sensor 120 is attached) within the moving image. The sensor-attached body part to which acceleration sensor 120 is attached moves within the moving image along with the motion of test subject 200 or the movement of video camera 130. Accordingly, coordinate transformer 41 performs coordinate transformation of motion trajectory 220, for example, for each frame of the moving image.

Superimposer 40 superimposes, on the moving image, motion trajectory 220 that has been coordinate-transformed. At this time, superimposer 40 enlarges motion trajectory 220 and thereafter superimposes motion trajectory 220 on the moving image. That is, the scale of test subject 200 imaged on the moving image and the scale of motion trajectory 220 are different. In the present embodiment, because acceleration sensor 120 is attached to the waist of test subject 200, with motion trajectory 220, the movement of the waist is displayed to be larger than the movement of the waist imaged on the moving image.

Figure 5:
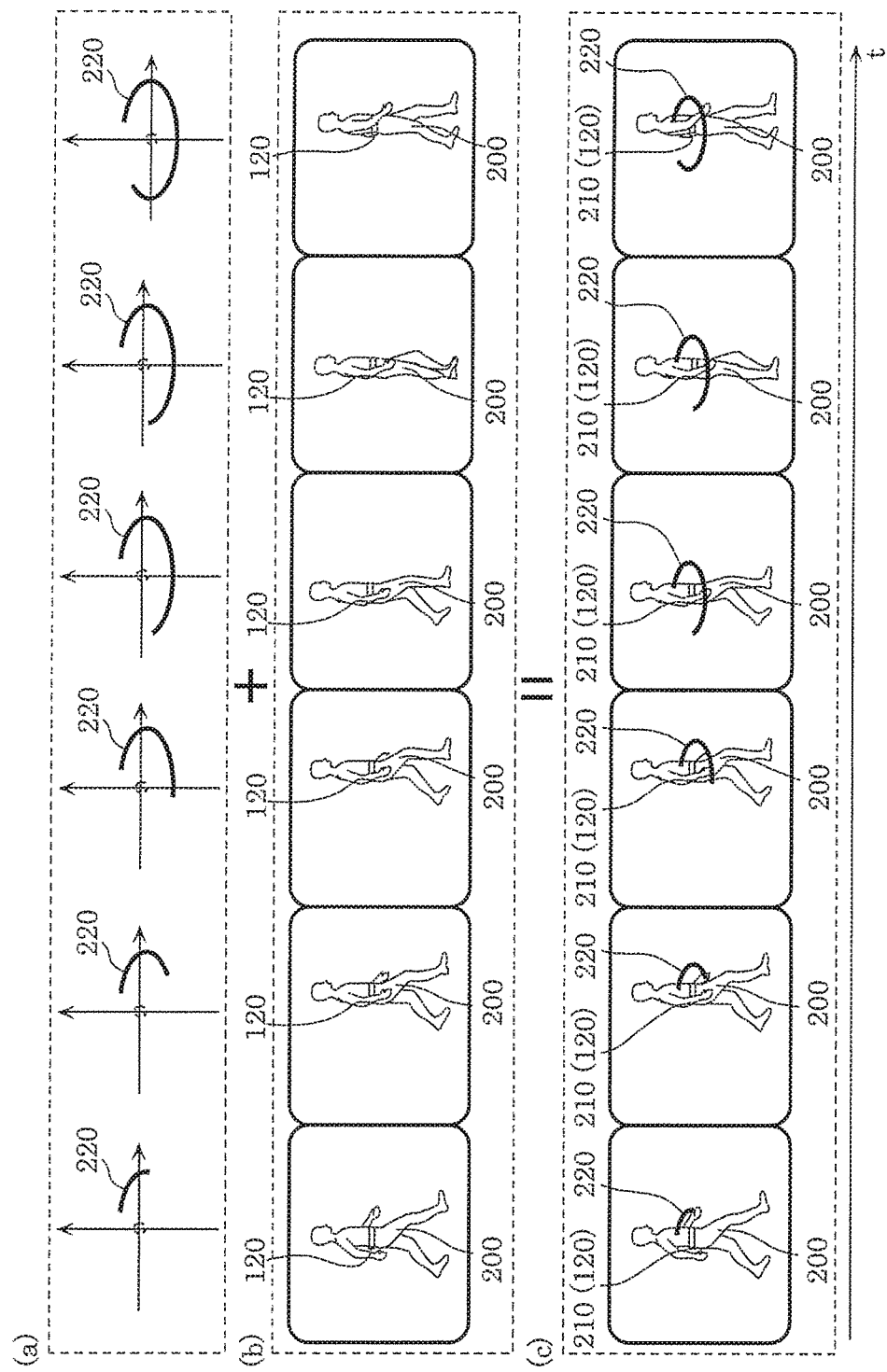
FIG. 5 is a diagram showing superimposition processing performed by a superimposer according to Embodiment 1.

FIG. 5 is a diagram showing superimposition processing performed by superimposer 40 according to the present embodiment. To be specific, (a) in FIG. 5 shows motion trajectory 220 generated based on the acceleration detected by acceleration sensor 120. (b) in FIG. 5 shows a moving image imaged by video camera 130. (c) in FIG. 5 shows a moving image on which motion trajectory 220 is superimposed.

As shown in FIG. 5, in the generated moving image, origin point 210 of motion trajectory 220 is present at the position of the sensor-attached body part to which acceleration sensor 120 is attached. That is, origin point 210 of motion trajectory 220 also moves along with the movement of the position of the sensor-attached body part to which acceleration sensor 120 is attached.

Here, motion trajectory 220 may be updated every predetermined period or timing. As used herein, the term "update" refers to an operation of deleting the previous trajectory and rendering a new trajectory. For example, motion trajectory 220 is updated according to the walking motion of test subject 200. To be specific, motion trajectory 220 is updated each time test subject 200 takes a step of walking. With this configuration, the motion trajectory of each step of walking can be easily recognized.

On the other hand, motion trajectory 220 may not be updated. With this configuration, the motion trajectory is continuously displayed within the moving image, and thus a walking motion of test subject 200 can be continuously recognized.

In the present embodiment, superimposer 40 is computer 140. Computer 140 includes a non-volatile memory in which a program is stored, a volatile memory that is a temporary storage area for executing a program, input/output ports, a processor for executing a program, and the like.

[Display]

Display 50 displays the moving image on which motion trajectory 220 is superimposed by superimposer 40. In the present embodiment, display 50 is display 150. Display 150 is, for example, LCD (Liquid Crystal Display), or the like.

[Operation]

Figure 6:
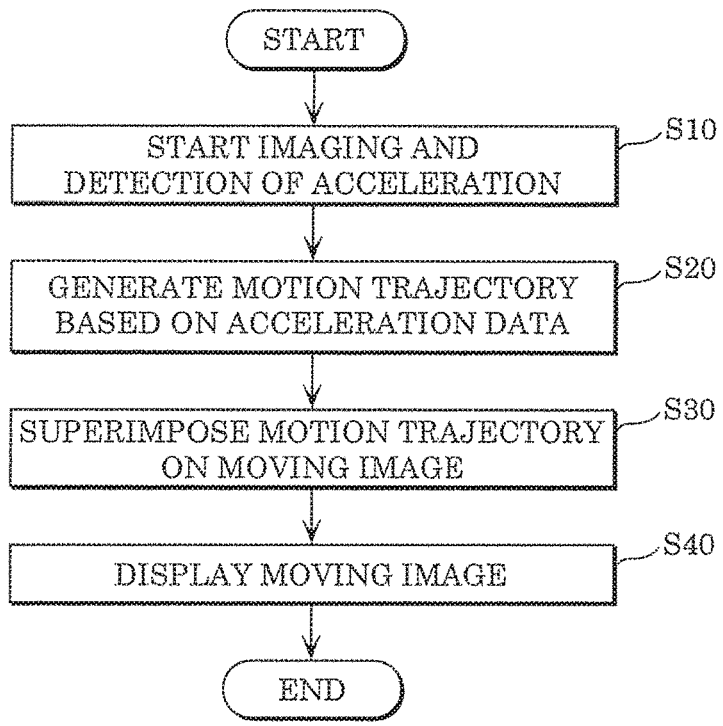
FIG. 6 is a flowchart illustrating operations performed by the motion display system according to Embodiment 1.

FIG. 6 is a flowchart showing operations performed by motion display system 1 according to the present embodiment.

First, imaging by video camera 130 and acceleration detection by acceleration sensor 120 are started (S10). In response thereto, computer 140 sequentially receives input of a moving image (image data of each frame) imaged by video camera 130 and acceleration data generated by acceleration sensor 120.

Next, superimposer 40 (computer 140) generates a motion trajectory based on the acceleration data (S20). To be specific, superimposer 40 calculates, based on the acceleration, the amount of displacement from the reference position and the direction of displacement. Superimposer 40 generates, for example, motion trajectory 220 as shown in FIG. 4 or (a) in FIG. 5.

Next, superimposer 40 superimposes motion trajectory 220 on the moving image (S30). To be specific, coordinate transformer 41 coordinate-transforms motion trajectory 220 such that origin point 210 of the coordinate system of motion trajectory 220 matches the position of the sensor-attached body part to which acceleration sensor 120 is attached within the moving image.

Next, display 50 displays the moving image on which motion trajectory 220 is superimposed (S40).

The processing described above is performed, for example, for each frame of the moving image. To be specific, superimposer 40 superimposes motion trajectory 220 corresponding to the time of a frame of the moving image on the frame. Superimposer 40 stops the superimposition processing if a frame of the moving image is not input.

With this configuration, the moving image on which motion trajectory 220 is superimposed can be displayed on display 150 in real time according to the motion of test subject 200. Because motion trajectory 220 is superimposed on the moving image in which the motion of test subject 200 is imaged, the motion of test subject 200 can be easily visually recognized.

Motion trajectory 220 may be superimposed on the moving image, instead of real time, at the time when the moving image is reproduced, by storing the time-series acceleration data acquired from acceleration sensor 120 and the moving image imaged by video camera 130. In this case, acceleration sensor 120 need not have a wireless communication function. For example, acceleration sensor 120 may include a memory for storing the time-series acceleration data, the memory being a memory that can be read by computer 140.

Advantageous Effects, Etc

As described above, motion display system 1 according to the present embodiment includes: acceleration sensor 120 that detects an acceleration of a predetermined body part of test subject 200; imager 30 that images a motion of test subject 200 and generates a moving image; identifier 10 that is attached to test subject 200 to determine a position of the body part; superimposer 40 that superimposes motion trajectory 220 of the body part generated based on the acceleration detected by acceleration sensor 120 on a position of the body part determined based on identifier 10 within the moving image generated by imager 30 in synchronization with the moving image; and display 50 that displays the moving image on which motion trajectory 220 is superimposed by superimposer 40.

As described above, motion display system 1 not only detects the acceleration of the body part with the use of acceleration sensor 120, but also generates a moving image by imaging the motion of test subject 200. Accordingly, by associating the time information of the time-series acceleration data and the time information of the moving image with each other, it is possible to associate the acceleration data with each frame of the moving image. Also, the amount of displacement of the body part can be calculated based on the acceleration data, and thus motion trajectory 220 of the body part can be associated with the moving image.

Accordingly, by superimposing motion trajectory 220 on the moving image, it is possible to simultaneously view the motion and posture of test subject 200 and motion trajectory 220 of the body part. According to a conventional technique, the moving image and the motion trajectory are displayed separately, which requires the viewer to move the direction of the eyes between the moving image and the motion trajectory in order to view the motion of the test subject. In contrast, according to the present embodiment, because motion trajectory 220 is superimposed on the moving image, the viewer does not need to move the direction of the eyes, and can easily visually recognize the motion of test subject 200.

At this time, because motion display system 1 includes identifier 10, the position of identifier 10 within the moving image can be easily detected. Accordingly, because the position of the sensor-attached body part to which acceleration sensor 120 is attached within the moving image can be easily determined, motion trajectory 220 can be superimposed based on the position of the sensor-attached body part.

As means for generating motion trajectory 220, it may be possible to use image processing on the moving image generated by video camera 130. However, when motion trajectory 220 is generated by using the moving image, it becomes difficult to detect a variation in movement of the body part through image processing as the distance between video camera 130 and test subject 200 becomes longer. That is, the generation of motion trajectory based on the moving image has a low degree of freedom of measurement.

In contrast, motion display system 1 utilizes, instead of the moving image, the acceleration data detected by the acceleration sensor in order to generate motion trajectory 220. Accordingly, if, for example, computer 140 including superimposer 40 is located within a wireless communication coverage range of acceleration sensor 120, motion trajectory 220 of the body part can be generated with high accuracy based on the acceleration data. Thus, according to the present embodiment, it is possible to implement motion display system 1 having a high degree of freedom of measurement.

Also, for example, superimposer 40 includes coordinate transformer 41 that coordinate-transforms motion trajectory 220 such that a specific point in the coordinate system of motion trajectory 220 is set to the fixed point of test subject 200 within the moving image, and superimposer 40 superimposes coordinate-transformed motion trajectory 220 on the moving image.

With this configuration, coordinate transformation is performed such that a specific point in the coordinate system of motion trajectory 220 is set to the fixed point within the moving image, and thus for example, the reference point on motion trajectory 220 can be aligned with the sensor-attached body part to which acceleration sensor 120 is attached within the moving image. Accordingly, the association between motion trajectory 220 and the motion of test subject 200 within the moving image can be made more visually recognizable.

Also, for example, the specific point is origin point 210 of the coordinate system of motion trajectory 220, and the fixed point is the position of the body part within the moving image.

As described above, origin point 210 of the coordinate system of motion trajectory 220 can be aligned with the sensor-attached body part to which acceleration sensor 120 is attached within the moving image, and thus the association between motion trajectory 220 and the motion of test subject 200 within the moving image can be made more visually recognizable.

Also, for example, the relative position of identifier 10 with respect to the body part is fixed, and coordinate transformer 41 determines the fixed point within the moving image based on the position of identifier 10 within the moving image, and then coordinate-transforms motion trajectory 220 such that the specific point is set to the fixed point that has been determined.

With this configuration, the sensor-attached body part to which acceleration sensor 120 is attached within the moving image is determined based on the positional relationship between identifier 10 and the sensor-attached body part to which acceleration sensor 120 is attached. Accordingly, identifier 10 and acceleration sensor 120 may be attached to different body parts. For this reason, for example, even in the case where acceleration sensor 120 fails to be imaged due to the motion of test subject 200, the sensor-attached body part to which acceleration sensor 120 is attached can be determined based on the position of identifier 10. Accordingly, it is possible to increase the degree of freedom of the sensor-attached body part to which acceleration sensor 120 is attached, and increase the degree of freedom of measurement.

Also, for example, identifier 10 is a color marker or a reflector.

With this configuration, the position of identifier 10 within the moving image can be extracted with high accuracy, and it is therefore possible to highly accurately determine the position of acceleration sensor 120.

The technique according to the present embodiment can be implemented not only as motion display system 1, but also as a program for causing a computer to function as motion display system 1 described above. Alternatively, the technique according to the present embodiment can also be implemented as a recording medium in which the program is recorded, such as a computer-readable DVD (Digital Versatile Disc).

That is, the above-described generic or specific aspects of the present disclosure may be implemented by a system, an apparatus, an integrated circuit, a computer program or a computer readable recording medium, or may be implemented by any combination of a system, an apparatus, an integrated circuit, a computer program and a recording medium.

(Variation)

The embodiment given above has been described by taking an example in which only one identifier 10 (reflector 110) is provided, but the present disclosure is not limited thereto. The motion display system may include a plurality of identifiers. The plurality of identifiers are attached to different body parts of test subject 200. In the present variation, the plurality of identifiers are attached at opposing positions across the test subject.

Figure 7:
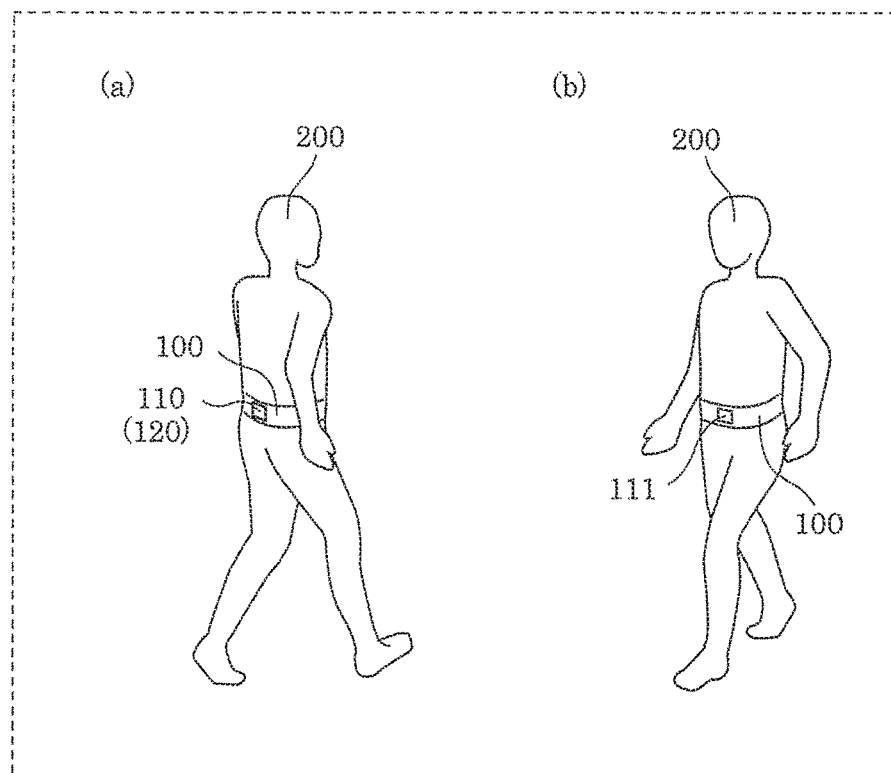
FIG. 7 is a diagram showing a test subject to which an acceleration sensor according to a variation of Embodiment 1 is attached.

FIG. 7 shows test subject 200 to which acceleration sensor 120 according to the present variation is attached. To be specific, (a) in FIG. 7 shows the back side of test subject 200, and (b) in FIG. 7 shows the front side of test subject 200.

As shown in FIG. 7, two reflectors 110 and 111 are respectively provided on the back side and the front side of test subject 200.

Two reflectors 110 and 111 are each fixed in a relative positional relationship with respect to the sensor-attached body part to which acceleration sensor 120 is attached. For example, reflector 110 is provided on the outer surface of acceleration sensor 120. That is, reflector 110 is provided at the position of the sensor-attached body part to which acceleration sensor 120 is attached.

Reflector 111 is provided on the opposite side of reflector 110 across test subject 200. For example, the distance between two reflectors 110 and 111, and the direction from reflector 110 to reflector 111 are determined in advance. Coordinate transformer 41 acquires the direction from reflector 110 to reflector 111, and the distance between reflectors 110 and 111 based on user input, a still image of test subject 200, or the like.

In the present variation, superimposer 40 determines the position of at least one of two reflectors 110 and 111 in the moving image. Accordingly, superimposer 40 can determine the position of sensor-attached body part to which acceleration sensor 120 is attached based on the determined position of the reflector.

For example, in the case where the motion of test subject 200 is imaged by panning the camera, reflector 110 (identifier 10) is not necessarily constantly imaged. There may be a case where reflector 110 is hidden by another body part (for example, arm) of test subject 200, and cannot be imaged.

In this case, for example, the position of reflector 110 imaged in a frame may be estimated through interpolation processing or the like based on the position of reflector 110 imaged in the previous frame and that in the subsequent frame. If the period during which reflector 110 is not imaged is short such as only for a moment, highly accurate estimation is possible.

However, if, for example, reflector 110 is not imaged for a long period of time, it is not possible to estimate the accurate position of reflector 110, which makes it difficult to determine the reference position used to superimpose motion trajectory 220.

However, the motion display system according to the present variation includes a plurality of identifiers 10, and the plurality of identifiers 10 are provided at opposing positions across test subject 200.

With this configuration, because the motion display system includes a plurality of identifiers 10, as long as one of the plurality of identifiers 10 is imaged in the moving image, it is possible to determine the sensor-attached body part to which acceleration sensor 120 is attached. For example, even in the case where reflector 110 fails to be imaged, the sensor-attached body part to which acceleration sensor 120 is attached can be determined based on the position of reflector 111. Accordingly, it is possible to superimpose motion trajectory 220 with high accuracy.

In addition, it is unnecessary to constantly image one identifier 10, and it is therefore possible to increase the degree of freedom of imaging by video camera 130. Accordingly, the degree of freedom of measurement can be increased.

Embodiment 2

A motion display system according to Embodiment 2 will be described next.

The motion display system according to the present embodiment is different from motion display system 1 according to Embodiment 1 in that the motion trajectory is expressed in a three-dimensional coordinate system whereas the motion trajectory is expressed in a two-dimensional coordinate system in motion display system 1 according to Embodiment 1. Also, in the motion display system according to the present embodiment, correction is performed according to the attachment position of acceleration sensor 120. Hereinafter, the present embodiment will be described focusing on differences from Embodiment 1, and a description of the same configuration as that of Embodiment 1 may be omitted or simplified.

Figure 8:
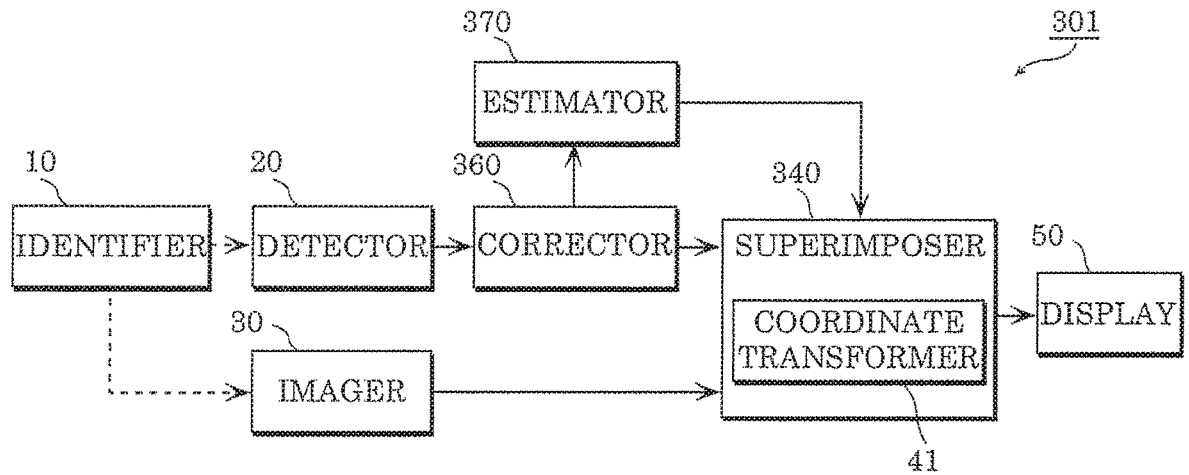
FIG. 8 is a block diagram showing a functional configuration of a motion display system according to Embodiment 2.

FIG. 8 is a block diagram showing a functional configuration of motion display system 301 according to the present embodiment. As shown in FIG. 8, motion display system 301 is different from motion display system 1 according to Embodiment 1 shown in FIG. 1 in that motion display system 301 includes superimposer 340 instead of superimposer 40, and further includes corrector 360 and estimator 370.

Superimposer 340 superimposes a motion trajectory of the body part expressed in a three-dimensional coordinate system on the position of the body part within the moving image. In the present embodiment, superimposer 340 superimposes the motion trajectory in the three-dimensional coordinate system that has been corrected by corrector 360. Specific processing is the same as that performed by superimposer 40 according to Embodiment 1 except that the motion trajectory in the three-dimensional coordinate system that has been corrected by corrector 360 is used instead of the motion trajectory in the two-dimensional coordinate system.

Figure 9:
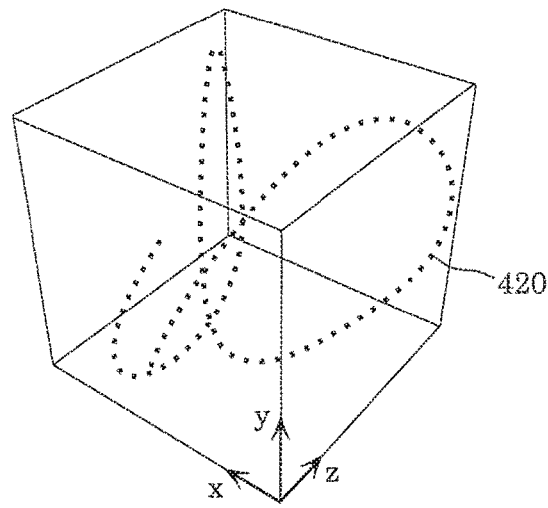
FIG. 9 is a diagram showing a motion trajectory of a predetermined body part in a three-dimensional coordinate system generated based on acceleration data detected by an acceleration sensor according to Embodiment 2.

FIG. 9 is a diagram showing motion trajectory 420 in a three-dimensional coordinate system of the predetermined body part generated based on the acceleration data detected by acceleration sensor 120 according to the present embodiment. In FIG. 9, motion trajectory 420 is indicated by a thick dotted line, and the axes (x axis, y axis, and z axis) are indicated by thin solid lines. By projecting motion trajectory 420 in the three-dimensional coordinate system shown in FIG. 9 to any one of a horizontal plane (xz plane), a coronal plane (xy plane), and a sagittal plane (yz plane), the motion trajectory in the two-dimensional coordinate system described in Embodiment 1 can be obtained.

Corrector 360 generates motion trajectory 420 in the three-dimensional coordinate system based on the three-dimensional acceleration data detected by acceleration sensor 120. In the present embodiment, corrector 360 corrects a deviation of the motion trajectory (motion trajectories 421 and 422 shown in FIG. 11) when acceleration sensor 120 is not attached to the correct position. To be specific, corrector 360 corrects an inclination of the motion trajectory with respect to the reference direction.

Estimator 370 estimates the right and left motions of walking of the test subject. To be specific, estimator 370 estimates a typical motion of walking of the test subject based on the motion trajectory corrected by corrector 360. Examples of the typical motion include heel contact, foot flat, mid-stance, heel off, toe off, mid-swing, and the like.

Estimator 370 estimates the right and left motions of walking of the test subject by integrating the areas of a plurality of micro-triangles that constitute motion trajectory 420. The estimation processing will be described later in detail.

Corrector 360 and estimator 370 include a non-volatile memory in which a program is stored, a volatile memory that is a temporary storage area for executing a program, input/output ports, a processor for executing a program, and the like.

[Correction of Inclination]

A description will now be given of the deviation of the motion trajectory when acceleration sensor 120 is not attached to the correct position.

Figure 10:
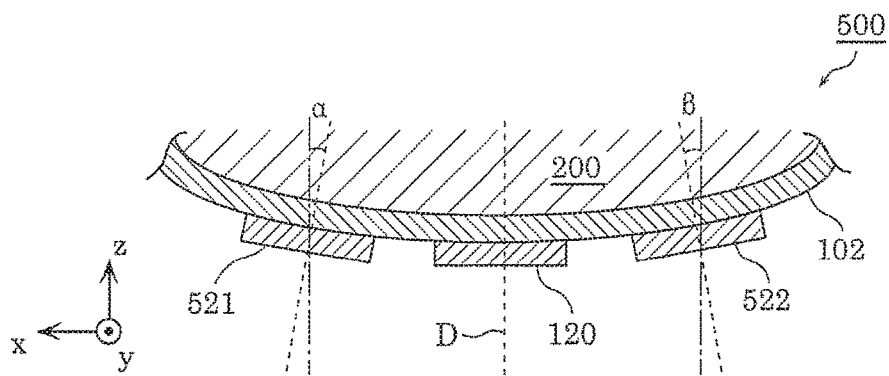
FIG. 10 is a diagram showing attachment positions on a horizontal plane of a plurality of acceleration sensors attached to a test subject in Embodiment 2.

FIG. 10 is a diagram showing attachment positions on a horizontal plane of a plurality of acceleration sensors attached to test subject 200 in the present embodiment. FIG. 10 shows a cross-sectional view of belt 500 worn around the waist of test subject 200, taken along the horizontal plane.

Acceleration sensor 120 according to the present embodiment is fixed to strap 102 of belt 500. With belt 500 being worn around the waist or the like of test subject 200, acceleration sensor 120 generates three-dimensional acceleration vector data of the body part (sensor-attached body part) to which acceleration sensor 120 is attached.

As shown in FIG. 10, acceleration sensors 521 and 522 are attached to the strap 102 of belt 500. Acceleration sensors 521 and 522 each have the same function as that of acceleration sensor 120, and they are different from acceleration sensor 120 only in that the attachment positions are different. To be specific, acceleration sensor 521 is provided at a position 6 cm deviated from acceleration sensor 120 toward the left. Acceleration sensor 522 is provided at a position 6 cm deviated from acceleration sensor 120 toward the right. Acceleration sensors 521 and 522 are acceleration sensors for verification that are provided to collect data when acceleration sensor 120 is not attached to the correct position.

In the present embodiment, the correct attachment position of acceleration sensor 120 is the center on the back side of the waist of test subject 200. Because belt 500 is wound around the waist of test subject 200, acceleration sensors 521 and 522 provided at deviated positions from the correct position are inclined with respect to reference direction D as shown in FIG. 10. Here, the inclination angles of acceleration sensors 521 and 522 will be respectively represented by α and ß.

Reference direction D is determined according to the orientation of acceleration sensor 120 attached to the correct position. For example, reference direction D is a direction perpendicular to a contact portion between acceleration sensor 120 and test subject 200. Here, acceleration sensor 120 is attached to the center on the back side of the waist of test subject 200, and thus reference direction D corresponds to the front rear direction (z axis direction) of test subject 200.

Figure 11:
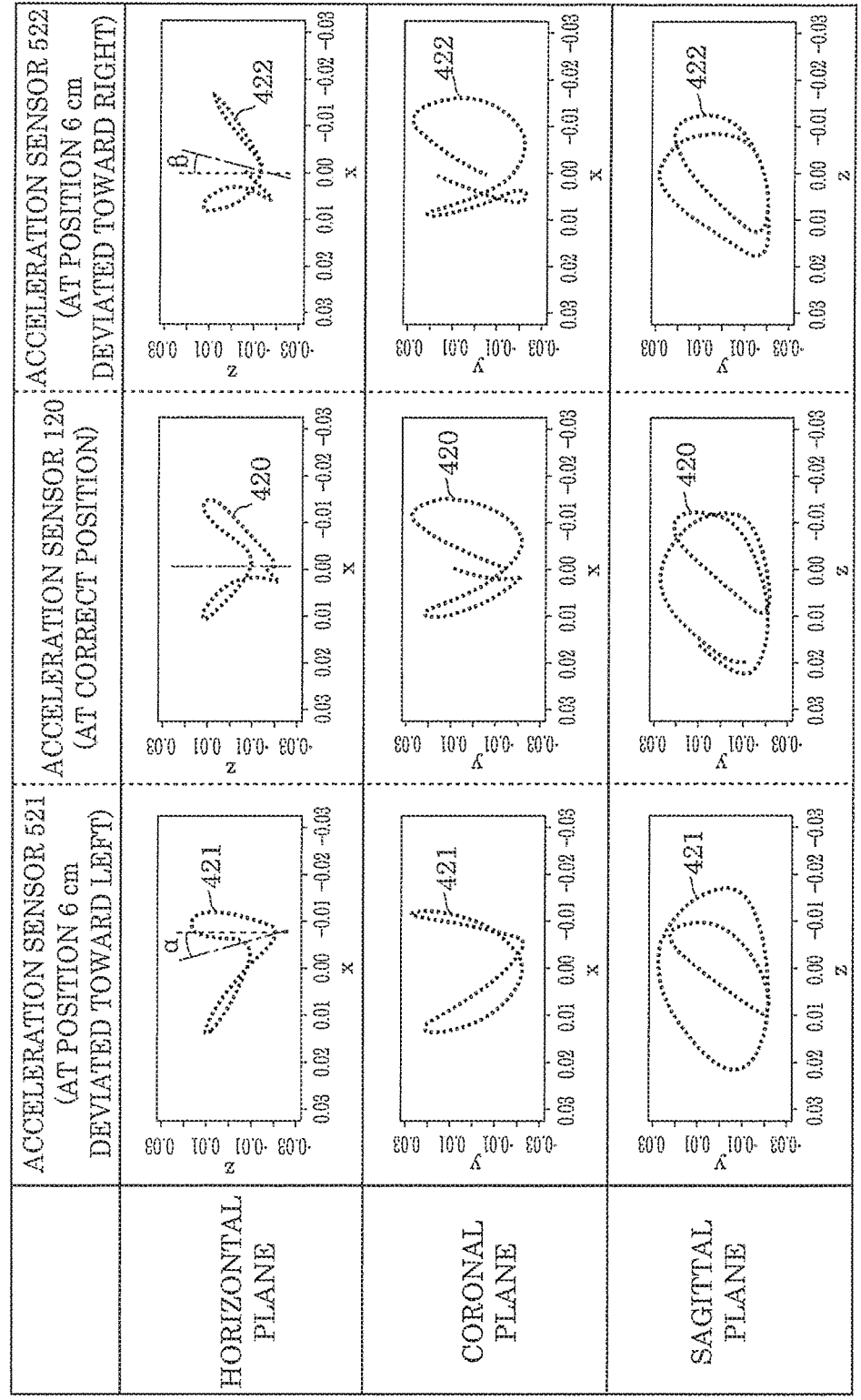
FIG. 11 is a diagram showing motion trajectories at different attachment positions of acceleration sensors according to Embodiment 2 that have been projected to a horizontal plane, a coronal plane, and a sagittal plane.

FIG. 11 is a diagram showing motion trajectories 420, 421, and 422 at different attachment positions of acceleration sensors 120, 521, and 522 according to the present embodiment that have been projected to a horizontal plane, a coronal plane, and a sagittal plane. As in Embodiment 1, motion trajectories 420, 421, and 422 are expressed in two-dimensional coordinate systems.

As shown in FIG. 11, motion trajectory 421 of acceleration sensor 521 provided at a position 6 cm deviated toward the left is equivalent to when motion trajectory 420 of acceleration sensor 120 attached to the correct position is inclined toward the left at inclination angle α. Likewise, motion trajectory 422 of acceleration sensor 522 provided at a position 6 cm deviated toward the right is equivalent to when motion trajectory 420 of acceleration sensor 120 attached to the correct position is inclined toward the right at inclination angle ß.

As shown in FIG. 11, motion trajectory 421 or 422 in the two-dimensional coordinate system generated based on acceleration sensor 521 or 522 has a collapsed shape as compared with motion trajectory 420 in the two-dimensional coordinate system generated based on acceleration sensor 120. This may cause an error in the result of estimation of the right and left motions by estimator 370.

To address this, in the present embodiment, corrector 360 corrects the inclination of motion trajectory 421 or 422 with respect to reference direction D. To be specific, corrector 360 rotates motion trajectory 421 or 422 by using a three-dimensional rotation matrix. Here, it is assumed that, for example, the coronal plane corresponds to xy plane, the horizontal plane corresponds to xz plane, and the sagittal plane corresponds to yz plane.

To be specific, coordinate values in a coordinate system (X, Y, Z) after correction can be represented by using coordinate values in a coordinate system (x, y, z) before correction. To be specific, the coordinate system (x, y, z) before correction is rotated about x axis by angle θ to obtain (x, Y', Z'), which is further rotated about Y' axis by angle Ψ to obtain (X', Y', Z). Furthermore, the coordinate system is rotated about Z axis by angle φ. The coordinate system thereby matches (X, Y, Z). Accordingly, the coordinate system (X, Y, Z) after correction can be expressed by Equation 1 given below.

[Math. 1]

$$\begin{pmatrix} X \\ Y \\ Z \end{pmatrix} = \begin{pmatrix} \cos\varphi & \sin\varphi & 0 \\ -\sin\varphi & \cos\varphi & 0 \\ 0 & 0 & 1 \end{pmatrix}$$ (Equation 1)

$$\begin{pmatrix} \cos\psi & 0 & -\sin\psi \\ 0 & 1 & 0 \\ \sin\psi & 0 & \cos\psi \end{pmatrix} \begin{pmatrix} 1 & 0 & 0 \\ 0 & \cos\theta & \sin\theta \\ 0 & -\sin\theta & \cos\theta \end{pmatrix} \begin{pmatrix} x \\ y \\ z \end{pmatrix}$$

For example, as in acceleration sensor 521 shown in FIG. 10, in the case where an inclination at angle α is observed on the horizontal plane, but no inclination is observed on the coronal plane and the sagittal plane, motion trajectory 421 can be corrected by substituting θ=0, Ψ=0, and φ=α into Equation 1 given above.

Figure 12:
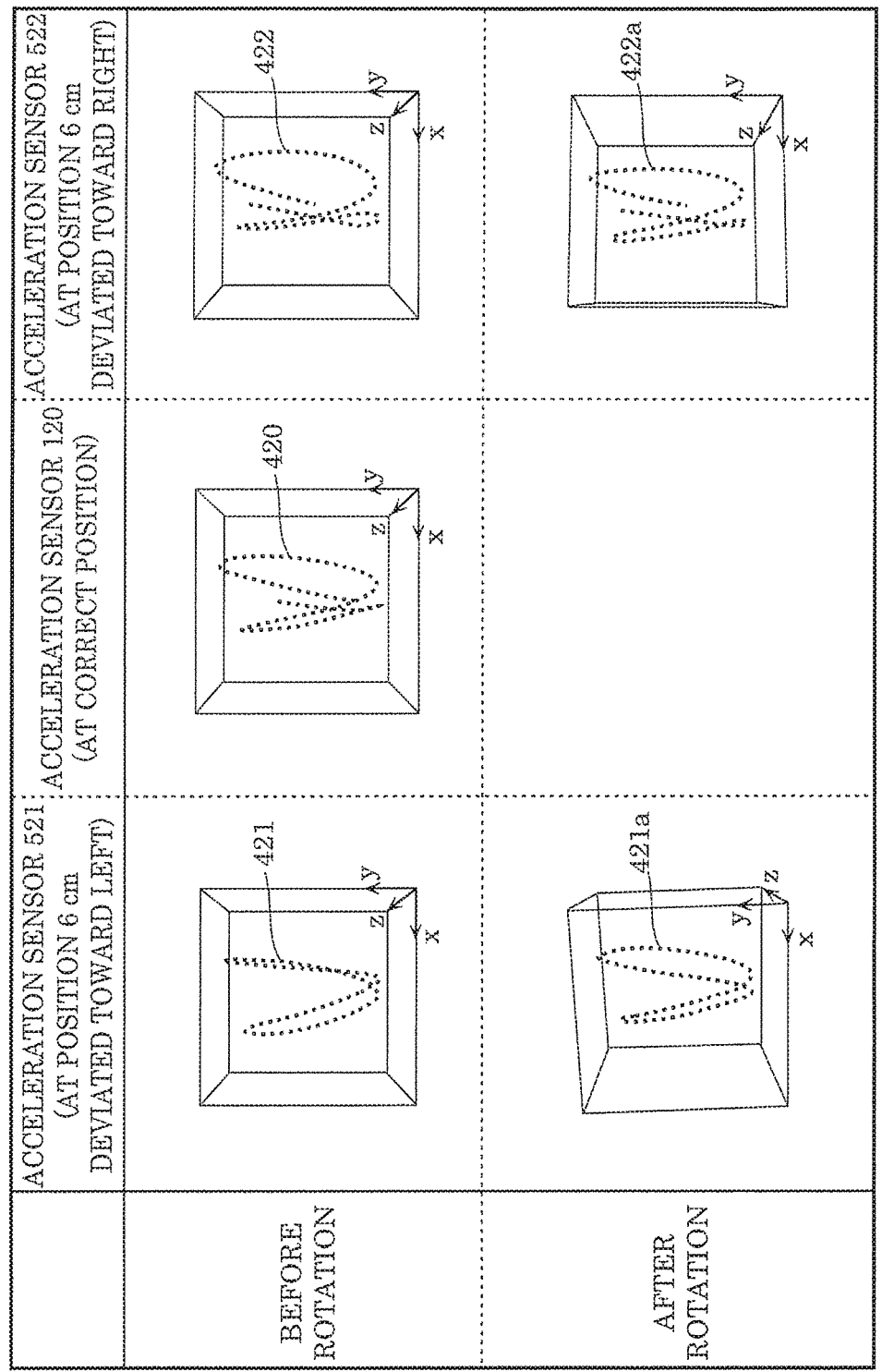
FIG. 12 is a diagram illustrating a motion trajectory correction performed by a corrector according to Embodiment 2.

FIG. 12 is a diagram illustrating a motion trajectory correction performed by corrector 360 according to the present embodiment. FIG. 12 is a diagram showing motion trajectories 420, 421, and 422 before rotation (i.e., before correction) as viewed from the coronal plane.

As shown in FIG. 12, motion trajectory 421 obtained from acceleration sensor 521 is rotated by an amount corresponding to inclination angle α. By doing so, rotated (i.e., corrected) motion trajectory 421a can be approximated to motion trajectory 420 obtained from acceleration sensor 120. Likewise, motion trajectory 422 obtained from acceleration sensor 522 is rotated by an amount corresponding to inclination angle ß. By doing so, rotated motion trajectory 422a can be approximated to motion trajectory 420 obtained from acceleration sensor 120.

Through this, even in the case where acceleration sensor 120 is not attached to the correct position, by correcting the motion trajectory based on the deviation from the correct attachment position, it is possible to generate a motion trajectory similar to that obtained in the case where acceleration sensor 120 is attached to the correct position.

[Estimation Processing]

Estimation processing for estimating a walking motion of test subject 200, which is performed by estimator 370, will now be described.

For example, as shown in FIG. 12, motion trajectory 420 generated based on the three-dimensional acceleration data detected by acceleration sensor 120 has a curve resembling a Lissajous curve when projected to the coronal plane. Estimator 370 estimates the balance between the right and left of walking of test subject 200 based on the ratio between the area on the left side of the Lissajous curve and the area on the right side of the same. For example, if the area on the left side and the area on the right side are equal, it can be estimated that test subject 200 is walking with a good balance between the right and left sides.

Figure 13:
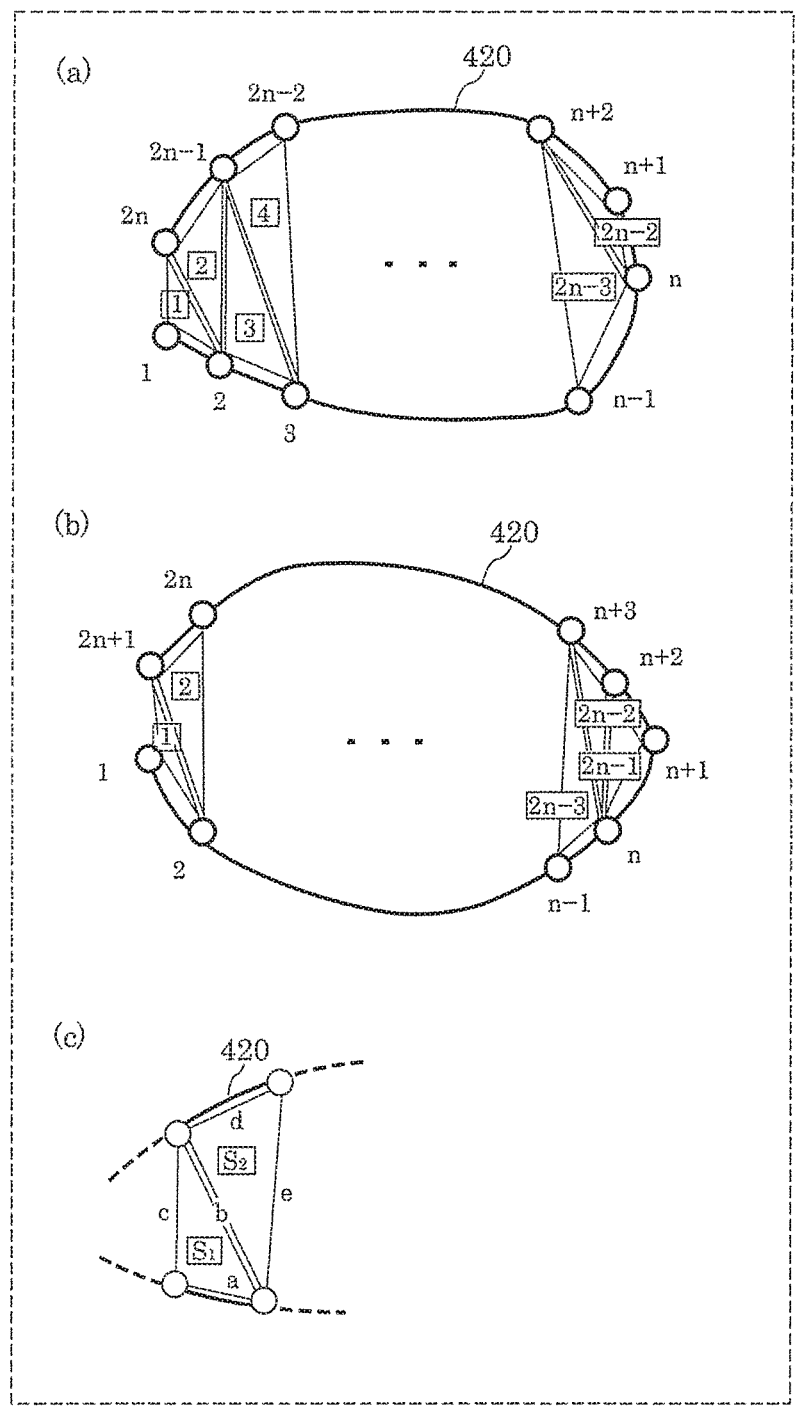
FIG. 13 is a diagram illustrating a method for calculating the area of a motion trajectory according to Embodiment 2.

Hereinafter, a method for calculating an area of a Lissajous curve will be described with reference to FIG. 13. FIG. 13 is a diagram illustrating a method for calculating an area of motion trajectory 420 according to the present embodiment. The area calculation method is different depending on whether the number N of measurement points takes an even number (2n) or an odd number (2n+1).

In FIG. 13, white circles indicate measurement points, and numerical values shown near the white circles indicate measurement point numbers. A thick solid line connecting the measurement points in numerical order corresponds to motion trajectory 420. Also, numerical values shown in triangles, each formed by a thin line connecting three measurement points, indicate triangle numbers. The numerical values indicating triangle numbers are shown in rectangles in order to distinguish them from the measurement point numbers.

<Case where Number N of Measurement Points Takes Even Number (2n)>

As shown in (a) in FIG. 13, with respect to measurement point 1 to measurement point n−1, estimator 370 determines the areas of triangles 2i−1 and 2i (i=n−1). The area of a triangle can be calculated based on the Heron's formula by using the length of each side. The length of each side of a triangle can be calculated from the coordinates of vertices of the triangle. Here, as shown in (c) in FIG. 13, triangles 2i−1 and 2i share one common side. Area S1 of triangle 2i−1 and area S2 of triangle 2i can be expressed by Equation 2 given below.

[Math. 2]

$$S1 = \sqrt{f1(f1-a)(f1-b)(f1-c)}$$
$$S2 = \sqrt{f2(f2-b)(f2-d)(f2-e)}$$
$$f1 = \frac{a+b+c}{2}$$
$$f2 = \frac{b+d+e}{2}$$

(Equation 2)

The total sum of the areas of triangles 1 to 2n−2 is the area on the left side (or the right side) of the Lissajous curve.

<Case where Number N of Measurement Points Takes Odd Number (2n+1)>

As shown in (b) in FIG. 13, with respect to measurement point 1 to measurement point n−1, estimator 370 determines the areas of triangles 2i−1 and 2i (i=n−1). To be specific, as in the case where number N takes an even number (2n), the areas can be calculated based on the Heron's formula. Furthermore, with respect to measurement point n, estimator 370 determines the area of triangle 2n−1. The total sum of the areas of triangles 1 to 2n−1 is the area on the left side (or the right side) of the Lissajous curve.

Advantageous Effects, Etc

As described above, in motion display system 301 according to the present embodiment, acceleration sensor 120 is a three-axis acceleration sensor, and superimposer 340 superimposes motion trajectory 420 of the body part expressed in the three-dimensional coordinate system.

With this configuration, because the motion trajectory expressed in the three-dimensional coordinate system is superimposed, the motion and posture of test subject 200 and the motion trajectory of the body part can be viewed simultaneously in three dimensions. Thus, the motion of test subject 200 can be easily visually recognized.

Also, for example, motion display system 301 further includes corrector 360 that corrects the inclination of the motion trajectory with respect to reference direction D, and superimposer 340 superimposes the motion trajectory that has been corrected by corrector 360.

With this configuration, even in the case where acceleration sensor 120 is not attached to the correct position, it is possible to obtain a motion trajectory similar to that obtained in the case where acceleration sensor 120 is attached to the correct position. Accordingly, it is possible to accurately identify the motion of the body part of test subject 200.

Also, for example, motion display system 301 further includes estimator 370 that estimates the right and left motions of walking of test subject 200 by integrating the areas of a plurality of micro-triangles that constitute motion trajectory 420.

With this configuration, it is possible to highly accurately perform the calculation of the areas of motion trajectory 420, and thus the right and left motions of walking of test subject 200 can be estimated with high accuracy.

(Others)

The motion display system according to the present disclosure has been described by way of the above embodiments and variations thereof, but the present disclosure is not limited to the embodiments and the like described above.

For example, in Embodiment 1 given above, an example was shown in which a specific point in the coordinate system of motion trajectory 220 is origin point 210 of the coordinate system of motion trajectory 220, but the present disclosure is not limited thereto. The specific point may be, for example, an intersection point where motion trajectory 220 intersects any one of x axis, y axis, and z axis, or an intersection point where motion trajectory 220 intersects any one of xy plane, yz plane, and xz plane. Alternatively, the specific point may be the center of gravity of motion trajectory 220, or the initial position of motion trajectory 220, Also, for example, in Embodiment 1 given above, imager 30, superimposer 40, and display 50 are implemented by video camera 130, computer 140, and display 150, but the present disclosure is not limited thereto. For example, the moving image on which motion trajectory 220 is superimposed may be displayed on a display included in video camera 130. That is, video camera 130 may function not only as imager 30, but may also function as superimposer 40 and display 50.

The present disclosure also encompasses other embodiments obtained by making various modifications that can be conceived by a person having ordinary skill in the art to the above embodiments as well as embodiments implemented by any combination of the structural elements and the functions of the above embodiments without departing from the scope of the present disclosure.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A motion display system, comprising:
an acceleration sensor that detects an acceleration of a body part of a test subject;
an imager that generates a moving image by imaging a motion of the test subject;
an identifier that is attached to the test subject to determine a position of the body part within the moving image; and
a superimposer that superimposes a motion trajectory of the body part generated based on the acceleration detected by the acceleration sensor on a position of the body part determined based on the identifier within the moving image generated by the imager in synchronization with the moving image;
a display that displays the moving image on which the motion trajectory is superimposed by the superimposer, wherein:
the superimposer superimposes the coordinate-transformed motion trajectory on the moving image,
the specific point is an origin point of the coordinate system of the motion trajectory,
the origin point matches with the fixed point of the test subject within the moving image, and moves along the movement of the fixed point within the moving image,
the acceleration sensor is a three-axis acceleration sensor,
the superimpose superimposes the motion trajectory of the body part expressed in a three-dimensional coordinate system, and
the motion display system further comprises an estimator that estimates right and left motions of walking of the test subject by integrating areas of a plurality of micro-triangles that constitute the motion trajectory.

2. The motion display system according to claim 1, the fixed point is a position of the body part within the moving image.

3. The motion display system according to claim 2, wherein the identifier is fixed in a relative position with respect to the body part, and
the coordinate transformer determines the fixed point within the moving image based on a position of the identifier within the moving image, and coordinate-transforms the motion trajectory such that the specific point is set to the fixed point that has been determined.

4. The motion display system according to claim 1, wherein the identifier comprises a plurality of identifiers, and
the plurality of identifiers are provided at opposing positions across the test subject.

5. The motion display system according to claim 1, wherein the identifier is one of a color marker and a reflector.

6. The motion display system according to claim 1, further comprising:
a corrector that corrects an inclination of the motion trajectory with respect to a reference direction,
wherein the superimposer superimposes the motion trajectory corrected by the corrector.

7. A non-transitory computer-readable recording medium having recorded thereon a program which when executed on a computer causes the computer to function as the motion display system according to claim 1.

8. A motion display system, comprising:
an acceleration sensor that detects an acceleration of a body part of a test subject;
an imager that generates a moving image by imaging a motion of the test subject;
an identifier that is attached to the test subject to determine a position of the body part within the moving image;
a superimposer that superimposes a motion trajectory of the body part generated based on the acceleration detected by the acceleration sensor on a position of the body part determined based on the identifier within the moving image generated by the imager in synchronization with the moving image;
an estimator that estimates right and left motions of walking of the test subject by integrating areas of a plurality of micro-triangles that constitute the motion trajectory; and
a display that displays the moving image on which the motion trajectory is superimposed by the superimposer, wherein:
the acceleration sensor is a three-axis acceleration sensor, and
the superimposer superimposes the motion trajectory of the body part expressed in a three-dimensional coordinate system.

* * * * *